United States Patent
Palermo (10) Patent No.: US 10,357,213 B2
(45) Date of Patent: Jul. 23, 2019

(54) POSITIONING AND RETAINING SYSTEM FOR INTRA-ORAL SENSORS

(71) Applicant: Dental Imaging Technologies Corporation, Hatfield, PA (US)

(72) Inventor: Adam T. Palermo, Philadelphia, PA (US)

(73) Assignee: DENTAL IMAGING TECHNOLOGIES CORPORATION, Hatfield, PA (US)

( * ) Notice: Subject to any disclaimer, the term of this patent is extended or adjusted under 35 U.S.C. 154(b) by 95 days.

(21) Appl. No.: 15/001,441

(22) Filed: Jan. 20, 2016

(65) Prior Publication Data

US 2017/0202526 A1 Jul. 20, 2017

(51) Int. Cl.
*A61B 6/14* (2006.01)
*A61B 6/04* (2006.01)
*G03B 42/04* (2006.01)

(52) U.S. Cl.
CPC ............ *A61B 6/145* (2013.01); *A61B 6/04* (2013.01); *G03B 42/042* (2013.01)

(58) Field of Classification Search
CPC .............................. A61B 6/145; G03B 42/042
See application file for complete search history.

(56) References Cited

U.S. PATENT DOCUMENTS

| | | | | |
|---|---|---|---|---|
| 2,782,317 A * | 2/1957 | Vacanti | ............... | G03B 42/042 378/168 |
| 2,899,559 A * | 8/1959 | Maurer | ............... | G03B 42/042 378/168 |
| 4,866,750 A * | 9/1989 | Chavarria | ............ | A61B 6/4435 378/168 |
| 4,965,885 A * | 10/1990 | Fuhrmann | ............ | G03B 42/042 378/168 |
| 5,677,537 A * | 10/1997 | Pfeiffer | .................... | A61B 1/05 378/170 |
| 6,540,399 B1 * | 4/2003 | Eppinger | ................. | A61B 6/14 378/167 |
| 2004/0096040 A1 * | 5/2004 | Kilcher | .................. | A61B 6/145 378/189 |
| 2007/0053498 A1 * | 3/2007 | Mandelkern | ........... | A61B 6/145 378/184 |
| 2008/0095321 A1 * | 4/2008 | Calderwood | .......... | A61B 6/145 378/170 |

FOREIGN PATENT DOCUMENTS

| | | |
|---|---|---|
| EP | 2807976 A1 | 12/2014 |
| JP | 2000102535 A | 4/2000 |
| JP | 2012183226 A | 9/2012 |
| WO | 2009/042203 A2 | 4/2009 |
| WO | 2011/106620 A2 | 9/2011 |

OTHER PUBLICATIONS

International Search Report and Written Opinion for Application No. PCT/US2017/014113 dated Mar. 21, 2017 (13 pages).
International Preliminary Report on Patentability for Application No. PCT/US2017/014113 dated Aug. 2, 2018 (5 pages).

* cited by examiner

Primary Examiner — Chih-Cheng Kao
(74) Attorney, Agent, or Firm — Michael Best & Friedrich LLP (57) ABSTRACT

A positioning and retaining system for intra-oral sensors includes a holder shaped to hold a curved intra-oral sensor, and a curved or flexible intra-oral sensor configured to be coupled to the holder.

14 Claims, 5 Drawing Sheets

POSITIONING AND RETAINING SYSTEM FOR INTRA-ORAL SENSORS

FIELD OF THE INVENTION

The present invention relates to sensors, in particular to intra-oral sensors for taking images of a patient's teeth.

BACKGROUND

Intra-oral sensors are commonly used to take images of a patient's teeth. In use, a patient bites down on a bite block, and an intra-oral sensor coupled to the bite block captures an image of the patient's teeth after being exposed to x-rays. Many current intra-oral sensors are both planar-shaped and rigid.

SUMMARY

Functional, rigid, planar-shaped intra-oral sensors do not always provide the comfort, accuracy, and/or precision that patients and dental professionals desire. Thus, there is a need for an improved system and method for positioning and retaining an intra-oral sensor in a patient's mouth. In accordance with one construction, a positioning and retaining system for an intra-oral sensor includes a holder shaped to hold a curved intra-oral sensor, and a curved or flexible intra-oral sensor configured to be coupled to the holder.

In accordance with another construction, a bite block for use in a dental setting includes a main body, and means for coupling a curved intra-oral sensor to the main body, wherein the means for coupling the curved intra-oral sensor is disposed in or coupled to the main body.

In accordance with another construction, a positioning and retaining system for an intra-oral sensor includes a holder having a main body, and at least one selected from a group consisting of a curved channel disposed on the holder, a plurality of fixed pins coupled to the main body, and a sliding block coupled to the main body.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Also, it is to be understood that the phraseology and terminology used herein is for the purpose of description and should not be regarded as limiting. The use of "including," "comprising" or "having" and variations thereof herein is meant to encompass the items listed thereafter and equivalents thereof as well as additional items. The terms "mounted," "connected" and "coupled" are used broadly and encompass both direct and indirect mounting, connecting and coupling. Further, "connected" and "coupled" are not restricted to physical or mechanical connections or couplings, and can include electrical connections or couplings, whether direct or indirect. Also, electronic communications and notifications may be performed using any known means including direct connections, wireless connections, etc.

Figure 1A:
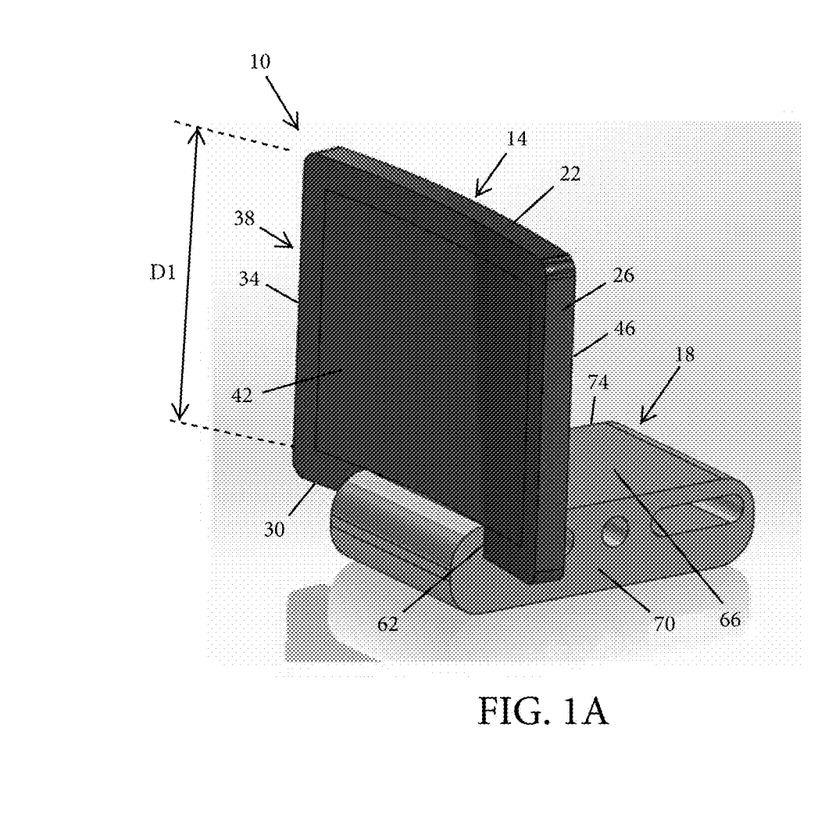
FIGS. 1A and 1B are perspective views of a positioning and retaining system according to one construction, including a holder having a curved channel, and an intra-oral sensor having a curved shape or capable of being bent into a curved shape that fits into the curved channel.
Figure 1B:
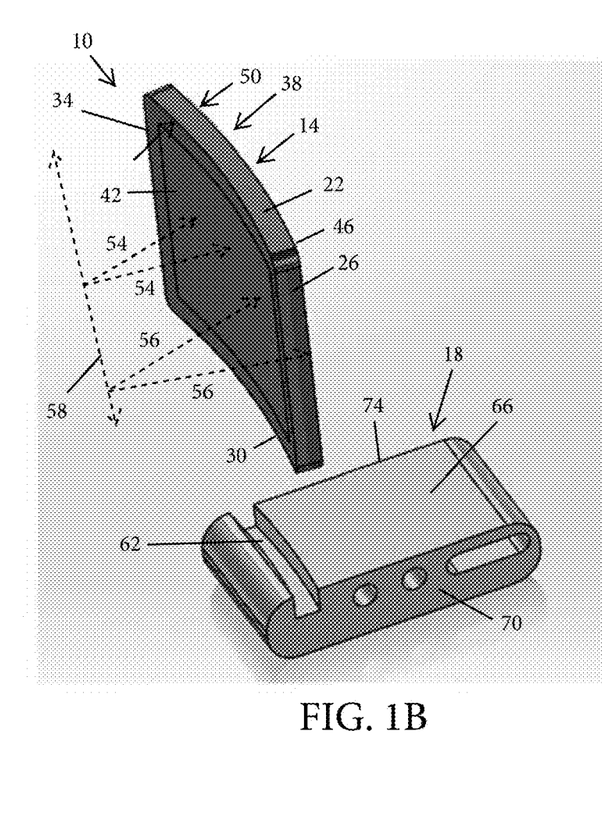

FIGS. 1A and 1B illustrate a positioning and retaining system 10. The positioning and retaining system 10 includes an intra-oral sensor 14 and a holder 18 for holding the intra-oral sensor 14.

In the illustrated construction, the intra-oral sensor 14 is made at least partially of a flexible material (e.g., a polymer) that permits the intra-oral sensor 14 to be bent and shaped into the curved shape illustrated in FIGS. 1A and 1B. For example, in some constructions the intra-oral sensor 14 is initially a bendable, planar intra-oral sensor that is then bent (e.g., with human fingers, a vice, or other suitable structure) to form the curved shape illustrated in FIGS. 1A and 1B. In other constructions, the intra-oral sensor 14 is a contoured, rigid sensor (formed for example of a harder polymer or plastic) that is already formed in the curved shape illustrated in FIGS. 1A and 1B during manufacturing of the intra-oral sensor 14.

In the illustrated construction, the intra-oral sensor 14 includes a first side surface 22, a second side surface 26, a third side surface 30, and a fourth side surface 34 that are connected to one another to define a perimeter 38 of the intra-oral sensor 14. The intra-oral sensor 14 also includes a concave surface 42, and a convex surface 46. The concave surface 42 and the convex surface 46 are each disposed within the perimeter 38. The concave surface 42 is disposed opposite the convex surface 46, such that a constant thickness 50 (FIG. 1B) extends between the concave surface 42 and the convex surface 46. The first side surface 22 and the third side surface 30 are curved, and the second side surface 26 and the fourth side surface 34 are generally rectangular. In the illustrated construction, the shape of the intra-oral sensor 14 can be defined as a cut-out piece of an imaginary cylinder.

As illustrated in FIG. 1B, the concave surface 42 has a radius of curvature 54 about an axis 58, and the convex surface 46 has a radius of curvature 56 about the axis 58. In the illustrated construction, the radius of curvature 54 as measured from the axis 58 can be, for example, constant at all points along the concave surface 42, and the radius of curvature 56 as measured from the axis 58 can be, for example, constant at all points along the convex surface 46. Optionally, the radius of curvature 54 or 56 can be the same as, approximately the same as, or slightly less than a radius of curvature of a maxillary arch or a mandibular arch in a patient's mouth, such that the intra-oral sensor 14 generally corresponds to the layout and pattern of a patient's teeth.

By corresponding to the layout and pattern of a patient's teeth, the intra-oral sensor 14 provides a better (e.g., more accurate) reading of the patient's teeth as compared with a planar or other-shaped intra-oral sensor. Additionally, the intra-oral sensor 14 is able to be held or positioned closer to more of the patient's teeth than with a planar or other-shaped intra-oral sensor, so that the intra-oral sensor 14 is less likely to obstruct other instruments that the dentist may wish to insert into the patient's mouth. Additionally, the shape of the intra-oral sensor 14 prevents the discomfort often associated with having a planar or other-shaped intra-oral sensor positioned in the patient's mouth.

Figure 1C:
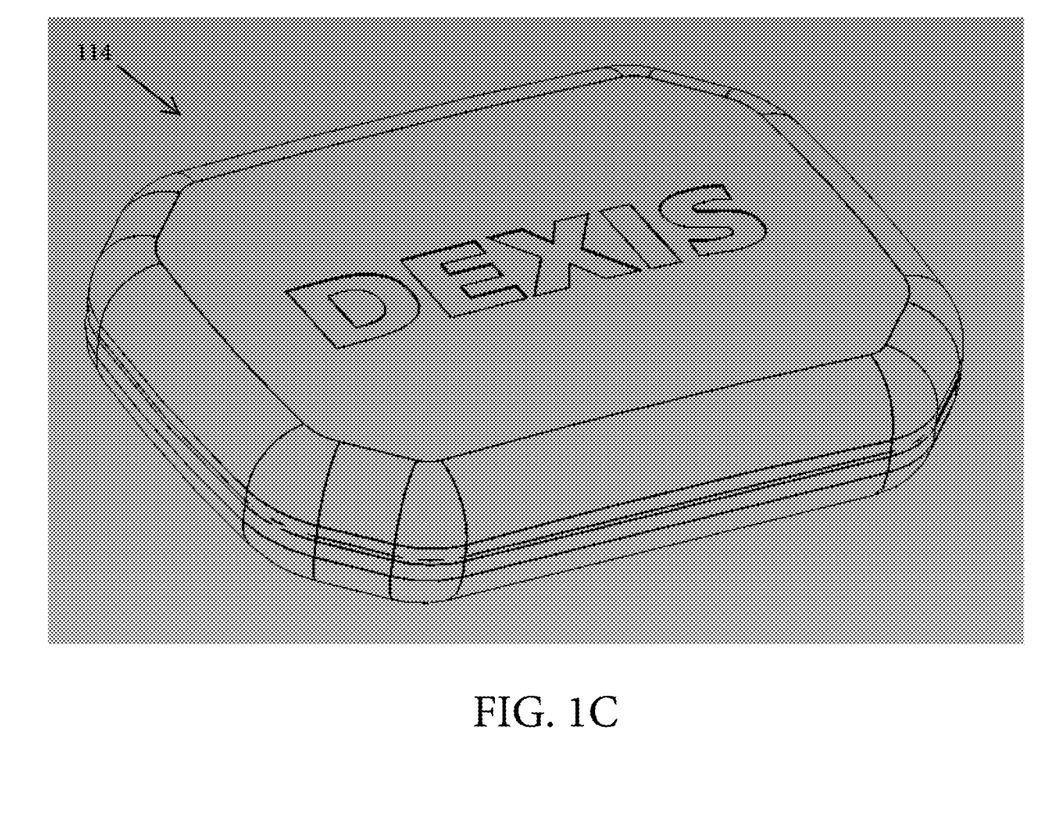
FIG. 1C is a perspective view of an eight-sided intra-oral sensor.

While the intra-oral sensor 14 in the illustrated construction has four side surfaces 22, 26, 30, and 34, in other constructions the intra-oral sensor 14 includes a different number of side surfaces. For example, in some constructions the intra-oral sensor 14 includes three side surfaces (e.g., a triangular sensor), or five side surfaces, or eight side surfaces (e.g., see FIG. 1C showing an intra-oral sensor 114 with eight side surfaces due to chamfered corners). Additionally, while the illustrated construction of the intra-oral sensor 14 includes a single concave surface 42 and a single convex surface 46, in other constructions other numbers of concave surfaces and convex surfaces are provided. For example, in some constructions the intra-oral sensor 14 includes two or more concave surfaces, or two or more convex surfaces. In some constructions, the intra-oral sensor 14 includes just a single convex surface and no concave surface, or vice versa.

While the intra-oral sensor 14 in the illustrated construction includes a single, constant radius of curvature 54, other constructions include different curvatures. For example, in some constructions the concave surface 42 includes at least two different radii of curvature, giving the concave surface 42 a more wave-like shape. In some constructions, the intra-oral sensor 14 is curved about more than the single axis 58. For example, in some constructions the intra-oral sensor 14 is curved about both the axis 58 as well as about an axis that is perpendicular to the axis 58, such that each of the first side surface 22, the second side surface 26, the third side surface 30, and the fourth side surface 34 have a curved shape, and the intra-oral sensor 14 takes on more of a cup-like shape. In some constructions, the intra-oral sensor 14 includes electronics or other hardware within a central region (or other region) of the intra-oral sensor 14, that prevents the center region from bending and being curved. Thus, in these embodiments, only portions of the intra-oral sensor 14 closer to the side surfaces 22, 26, 30, and 34 actually bend or otherwise have curvature. In some constructions, the intra-oral sensor 14 initially has one or more concave and/or convex surfaces that are straightened, or one or more sides that are straightened, when the intra-oral sensor 14 is bent and then held by the holder 18. Other constructions include various other shapes, curvatures, and sizes for the intra-oral sensor 14 than that illustrated in FIGS. 1A and 1B.

With continued reference to FIGS. 1A and 1B, and as described above, the intra-oral sensor 14 is coupled to a holder 18. In the illustrated construction, the holder 18 is a bite block. However, in other constructions the holder 18 is coupled to a separate bite block, or is merely a device for bending or maintaining the curved shape of the intra-oral sensor 14. In some constructions, the holder 18 is made of a polymer, although other constructions include different materials.

The holder 18 includes at least one feature or structure that receives the intra-oral sensor 14, and holds the intra-oral sensor 14 in place relative to the holder 18 (e.g., via a frictional fit or otherwise). For example, in the illustrated construction the holder 18 includes a channel 62. The channel 62 is a recess along a top surface 66 of the holder 18. The channel 62 extends from a first side wall 70 of the holder 18 to an opposite, second side wall 74 of the holder 18. The channel 62 has a curved shape that matches the curved shape of the intra-oral sensor 14, such that at least a portion of the intra-oral sensor 14 may be inserted into the channel 62. As illustrated in FIG. 1A, when the intra-oral sensor 14 is inserted into the channel 62, a portion of the intra-oral sensor 14 is disposed within the channel 62. The intra-oral sensor 14 extends generally perpendicularly relative to the holder 18.

With reference to FIG. 1A, the intra-oral sensor 14 extends above the holder 18 by a distance "D1" when the intra-oral sensor 14 is coupled to the holder 18. As illustrated in FIG. 1A, the distance "D1" is such that a majority of the intra-oral sensor 14 extends above the holder 18. However, in other constructions the distance "D1" is different than that shown. For example, in some constructions only approximately half of the intra-oral sensor 14 extends above the holder 18. In some constructions less than half of the intra-oral sensor 14 extends above the holder 18. Having more of the intra-oral sensor 14 disposed within the holder 18 aids in holding the intra-oral sensor 14 and maintaining the curved shape.

In use, the positioning and retaining system 10 is inserted into a patient's mouth, and the patient bites down on the holder 18 (e.g., on the top surface 66). When the patient bites down, the intra-oral sensor 14 remains behind the patient's teeth, with the shape of the intra-oral sensor 14 corresponding to the general layout and pattern of the patient's teeth. The intra-oral sensor 14 is used (e.g., with x-ray equipment) to take images of the patient's teeth. Once the images have been taken, the patient opens his or her mouth, and the positioning and retaining system 10 is removed.

Figure 2A:
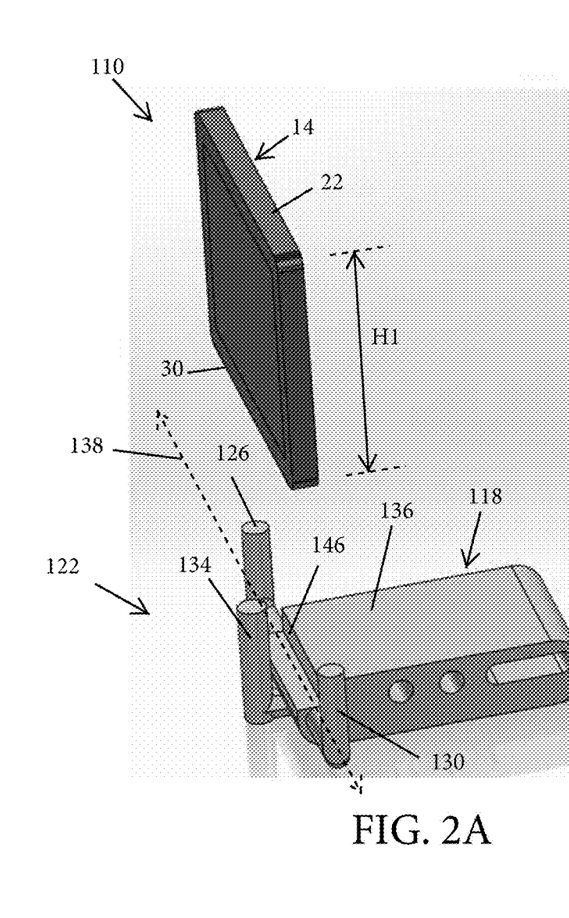
FIGS. 2A and 2B are perspective views of a positioning and retaining system according to another construction, including a holder having a fixed three-pin arrangement, and an intra-oral sensor having a curved shape or capable of being bent into a curved shape that fits into the three-pin arrangement.
Figure 2B:
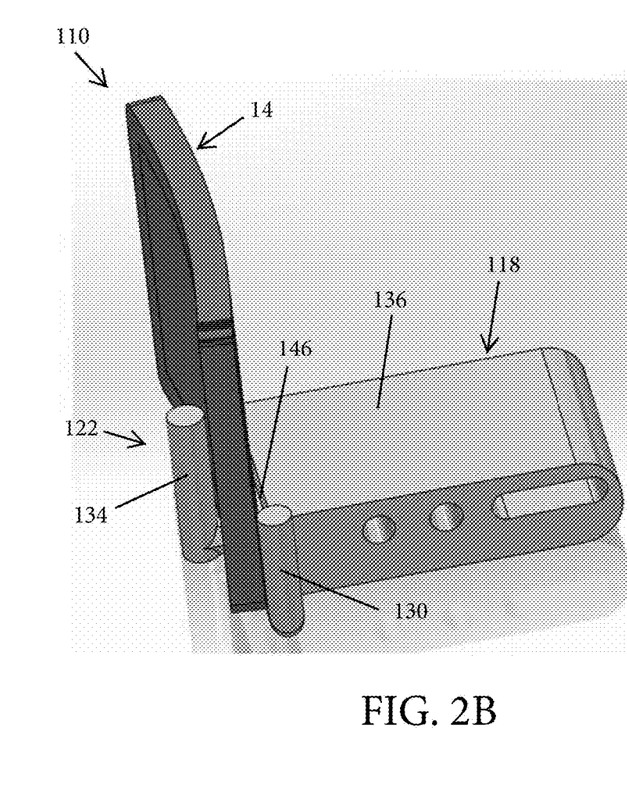

FIGS. 2A and 2B illustrate a positioning and retaining system 110 according to another construction. The positioning and retaining system 110 includes the same intra-oral sensor 14 as illustrated in FIGS. 1A and 1B, with a different holder 118 for holding the intra-oral sensor 14.

In the illustrated construction, the holder 118 is a bite block. However, in other constructions the holder 118 is coupled to a separate bite block, or is merely a device for bending or maintaining the curved shape of the intra-oral sensor 14. In some constructions, the holder 118 is made of a polymer, although other constructions include different materials.

The holder 118 includes at least one feature or structure that receives the intra-oral sensor 14, and holds the intra-oral sensor 14 in place relative to the holder 118 (e.g., via a frictional fit or otherwise). For example, in the illustrated construction the holder 118 includes a three-pin assembly 122 that is used to contact or press against at least three points or regions on the surface of the intra-oral sensor 14 and hold the intra-oral sensor 14 in place relative to the holder 118. With continued reference to FIG. 2A, in some constructions the intra-oral sensor 14 is initially a planar sensor but is flexible or bendable. The intra-oral sensor 14 can thus be bent (e.g., with human fingers, a vice, or any other suitable structure) to form the curved shape illustrated in FIG. 2B. In other constructions, the intra-oral sensor 14 is a contoured, rigid sensor (formed for example of a hard polymer) that is already formed already in the curved shape illustrated in FIG. 2B during manufacturing of the intra-oral sensor 14.

With continued reference to FIGS. 2A and 2B, the intra-oral sensor 14 is placed (e.g., pushed down) into the three-pin assembly 122. In the illustrated construction, the three-pin assembly 122 includes a first pin 126, a second pin 130, and a third pin 134, each of which is fixed on a main body 136 of the holder 118. The first and second pins 126, 130 can be aligned relative to one another along an axis 138. The third pin 134 is disposed between the first and second pins 126, 130 but is offset from axis 138. Optionally, a recessed portion 146 can be disposed between the first and second pins 126, 130, along the axis 138. As illustrated in FIG. 2B, when the intra-oral sensor 14 is placed into the three-pin assembly 122, the intra-oral sensor 14 is directed into the recessed portion 146. As the intra-oral sensor 14 (e.g., the side 30) approaches the recessed portion 146, the intra-oral sensor 14 fits between the three pins 126, 130, 134. When the intra-oral sensor 14 has been inserted into the three-pin assembly 122 (FIG. 2B), each of the pins 126, 130, 134 contacts and presses against the intra-oral sensor 14, maintaining the curved shape, and holding the intra-oral sensor 14 in place relative to the holder 118.

While the pins 126, 130, 134 are illustrated in FIG. 2B as extending along only a portion of the intra-oral sensor 14, in other constructions one or more of the pins 126, 130, 134 extends a different height. For example, and with reference to FIG. 2A, the intra-oral sensor 14 includes a height "H1" measured between the two side surfaces 22, 30. In some constructions one or more of the pins 126, 130, 134 extends along substantially the entire height "H1." Extending the pins 126, 130, 134 farther along the intra-oral sensor 14 in this manner aids in pressing and/or holding the intra-oral sensor 14 in its curved shape, and also in maintaining a consistent or uniform bend. In some constructions, one or more of the pins 126, 130, 134, or another structure on the holder 118 (e.g., a clip or structure), wraps at least partially around a portion of the intra-oral sensor 14, to further aid in holding the intra-oral sensor 14 in place relative to the holder 118.

In use, the positioning and retaining system 110 is inserted into a patient's mouth, and the patient bites down on the holder 118. When the patient bites down, the intra-oral sensor 14 remains behind the patient's teeth, with the shape of the intra-oral sensor 14 corresponding to the general layout and pattern of the patient's teeth. The intra-oral sensor 14 is used (e.g., with x-ray equipment) to take images of the patient's teeth. Once the images have been take, the patient opens his or her mouth, and the positioning and retaining system 110 is removed.

Figure 3A:
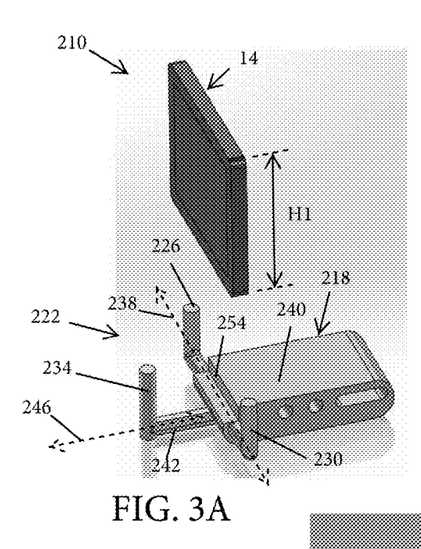
FIGS. 3A-C are perspective views of a positioning and retaining system according to another construction, including a three-pin arrangement having a sliding pin, and an intra-oral sensor having a curved shape or capable of being bent into a curved shape that is pressed by the sliding pin.
Figure 3B:
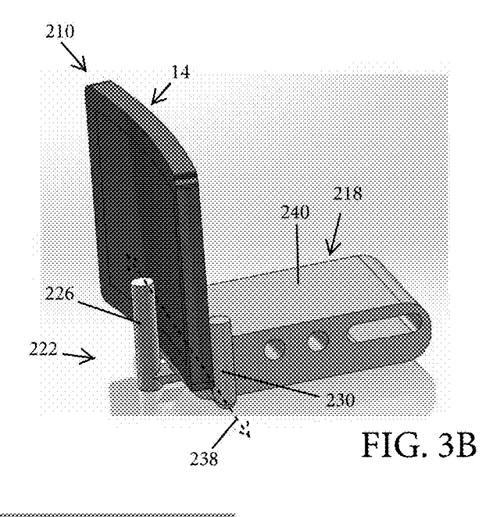
Figure 3C:
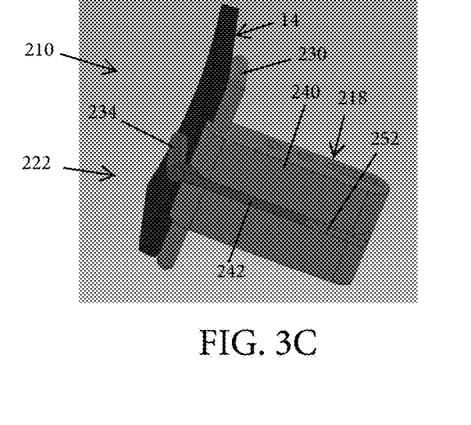

FIGS. 3A-C illustrate a positioning and retaining system 210 according to another construction. The positioning and retaining system 210 includes the same intra-oral sensor 14 as illustrated in FIGS. 1A and 1B, with a different holder 218 for holding the intra-oral sensor 14.

In the illustrated construction, the holder 218 is a bite block. However, in other constructions the holder 218 is coupled to a separate bite block, or is merely a device for bending or maintaining the curved shape of the intra-oral sensor 14.

The holder 218 includes at least one feature or structure that receives the intra-oral sensor 14, and holds the intra-oral sensor 14 in place relative to the holder 218 (e.g., via a frictional fit or otherwise). For example, in the illustrated construction the holder 218 includes a three-pin assembly 222 that is used to contact or press against at least three points along the intra-oral sensor 14 and to hold the intra-oral sensor 14 in place relative to the holder 218.

With continued reference to FIG. 3A, in the illustrated construction the intra-oral sensor 14 is initially a planar sensor. The three-pin assembly 222 includes a first pin 226, a second pin 230, and a third pin 234. The first and second pins 226, 230 are aligned relative to one another along an axis 238, and are fixed on a main body 240 of the holder 218. The third pin 234, however, is a sliding pin that is coupled to an arm 242 that is coupled to the main body 240. The arm 242 and the third pin 234 translate along an axis 246 that is perpendicular to the axis 238. In a fully retracted position (FIG. 3B), the third pin 234 is offset from axis 238. As illustrated in FIG. 3C, the main body 240 of the holder 218 includes a groove 252 that guides the arm 242.

With reference to FIG. 3A, a recessed portion 254 is disposed between the first and second pins 226, 230, along the axis 238. When the planar intra-oral sensor 14 is placed into the three-pin assembly 222, the intra-oral sensor 14 is directed toward the recessed portion 254. The arm 242 and the third pin 234 are then moved from the position illustrated in FIG. 3A to the position in FIG. 3B, where the intra-oral sensor 14 fits between the three pins 226, 230, 234, and where each of the three pins 226, 230, 234 contacts and presses against the intra-oral sensor 14, bending the intra-oral sensor 14 into the desired shape. In some constructions, and as noted above, the intra-oral sensor 14 is a rigid structure already contoured to have the radii of curvature 54, 56. In such a construction, the pin 234 does not bend the intra-oral sensor 14. Rather, the pins 226, 230, 234 act only to hold and retain the intra-oral sensor 14 relative to the holder 218.

While the pins 226, 230, 234 are illustrated in FIG. 3B as having heights extending along only a portion of the intra-oral sensor 14, in other constructions one or more of the pins 226, 230, 234 extends along a different height. For example, and with reference to FIG. 3A, in some constructions one or more of the pins 226, 230, 234 extends along substantially the entire height "H1" of the intra-oral sensor 14. In some constructions, one or more of the pins 226, 230, 234, or another structure on the holder 218 (e.g., a clip or structure), wraps at least partially around a portion of the intra-oral sensor 14, to further aid in holding the intra-oral sensor 14 in place relative to the holder 218.

In use, the positioning and retaining system 210 is inserted into a patient's mouth, and the patient bites down on the holder 218. When the patient bites down, the intra-oral sensor 14 remains behind the patient's teeth, with the shape of the intra-oral sensor 14 corresponding to the general layout and pattern of the patient's teeth. The intra-oral sensor 14 is used (e.g., with x-ray equipment) to take images of the patient's teeth. Once the images have been take, the patient opens his or her mouth, and the positioning and retaining system 210 is removed.

Figure 4A:
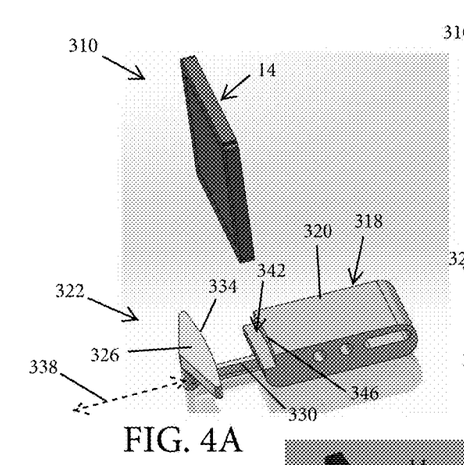
FIGS. 4A-C are perspective views of a positioning and retaining system according to another construction, including a holder having a sliding block, and an intra-oral sensor having a curved shape or capable of being bent into a curved shape that is pressed by the sliding block.
Figure 4B:
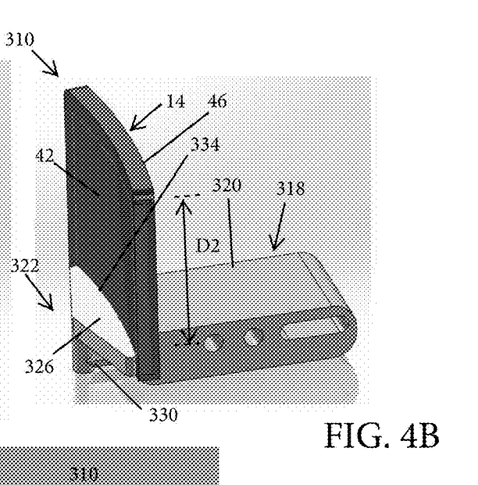
Figure 4C:
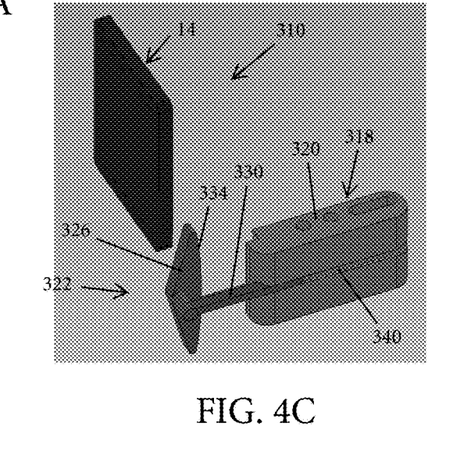

FIGS. 4A-C illustrate a positioning and retaining system 310 according to another construction. The positioning and retaining system 310 includes the same intra-oral sensor 14 as illustrated in FIGS. 1A and 1B, with a different holder 318 for holding the intra-oral sensor 14.

In the illustrated construction, the holder 318 is a bite block. However, in other constructions the holder 318 is coupled to a separate bite block, or is merely a device for bending or maintaining the curved shape of the intra-oral sensor 14.

The holder 318 includes at least one feature or structure that receives the intra-oral sensor 14, and holds the intra-oral sensor 14 in place relative to the holder 318 (e.g., via a frictional fit or otherwise). For example, in the illustrated construction the holder 318 includes a main body 320 and a movable block assembly 322 that is used to contact or press the intra-oral sensor 14 against the main body 320 to hold the intra-oral sensor 14 in place relative to the holder 318.

With continued reference to FIG. 4A, the movable block assembly 322 includes a sliding block 326 that is coupled to an arm 330. The sliding block 326 includes a convex surface 334. The arm 330 and the sliding block 326 translate along an axis 338 (FIG. 4A) relative to the main body 320. As illustrated in FIG. 4C, the main body 324 of the holder 318 includes a groove 340 that guides the arm 330.

With reference to FIG. 4A, a recessed portion 342 is disposed at one end of the holder 318. The recessed portion 342 defines a concave surface 346. In the illustrated construction, the intra-oral sensor 14 is initially planar. When the intra-oral sensor 14 is placed into the movable block assembly 322, the intra-oral sensor 14 is directed toward the recessed portion 342. The arm 330 and the block 326 are then moved from the position illustrated in FIG. 4A to the position in FIG. 4B, where the convex surface 334 contacts and presses against the intra-oral sensor 14, bending the intra-oral sensor 14 into the curved shape. In the illustrated construction the convex surface 334 has the same radius of curvature 54 as the concave surface 42 of the intra-oral sensor 14, and the concave surface 346 of the recessed portion 342 has the same radius of curvature 56 as the convex surface 46 of the intra-oral sensor 14. In some constructions, the intra-oral sensor 14 is a rigid structure already contoured to have the radii of curvature 54, 56. In such a construction, the sliding block 326 does not bend the intra-oral sensor 14. Rather, the convex surface 334 of the sliding block 326, in conjunction with the concave surface 346 of the recessed portion 342, act only to hold and retain the intra-oral sensor 14 relative to the holder 418.

With reference to FIG. 4B, the intra-oral sensor 14 extends above the holder 18 by a distance "D2" when the intra-oral sensor 14 is coupled to the holder 318. As illustrated in FIG. 4B, the distance "D2" is such that a majority of the intra-oral sensor 14 extends above the holder 318. However, in other constructions the distance "D2" is different than that shown. For example, in some constructions only approximately half of the intra-oral sensor 14 extends above the holder 318. In some constructions less than half of the intra-oral sensor 14 extends above the holder 318. Having more of the intra-oral sensor 14 disposed within the holder 318 aids in holding the intra-oral sensor 14 and maintaining the curved shape.

In use, the positioning and retaining system 310 is inserted into a patient's mouth, and the patient bites down on the holder 318. When the patient bites down, the intra-oral sensor 14 remains behind the patient's teeth, with the shape of the intra-oral sensor 14 corresponding to the general layout and pattern of the patient's teeth. The intra-oral sensor 14 is used (e.g., with x-ray equipment) to take images of the patient's teeth. Once the images have been take, the patient opens his or her mouth, and the positioning and retaining system 310 is removed.

Although the foregoing description has primarily emphasized the use of the intra-oral sensor 14 and the holders 18, 118, 218, 318 with taking x-ray images of human teeth, these components can also be used in conjunction with taking a variety of types of images, including but not limited to panoramic and/or cephalometric x-ray images of humans or animals.

Various features and advantages of the invention are set forth in the following claims.

What is claimed is:

1. A positioning and retaining system for an intra-oral sensor comprising:
   a holder shaped to hold a curved intra-oral sensor, the holder including a main body having a first end and a second, opposite end, a top surface, a bottom surface disposed opposite the top surface, a first side surface extending between the top and bottom surfaces, and a second side surface disposed opposite the first side surface and extending between the top and bottom surfaces, wherein the top and bottom surfaces at the second end are configured to be contacted and pressed by teeth during a dental procedure, wherein the holder further includes a recessed surface at the first end that is recessed relative to the top surface and is parallel to the top surface and defines a channel extending from the first side surface to the second side surface, wherein the channel curves about an axis that is perpendicular to both the top surface and the bottom surface, and wherein the channel is disposed between the axis and the second end.

2. The positioning and retaining system of claim 1, further comprising a curved intra oral sensor having a bottom surface configured to rest on the recessed surface, wherein the holder is configured to hold the curved intra-oral sensor via a frictional fit such that the intra-oral sensor is disposed adjacent the teeth when the teeth bite down on the top and bottom surfaces.

3. The positioning and retaining system of claim 2, wherein the curved intra-oral sensor includes a concave surface and an opposite, convex surface.

4. The positioning and retaining system of claim 3, wherein the concave surface has an essentially constant radius of curvature at a plurality of points along the concave surface.

5. The positioning and retaining system of claim 3, wherein the channel has a constant width, and wherein the intra-oral sensor has a constant thickness that corresponds to the constant width of the channel, wherein the thickness extends between the concave surface and the convex surface.

6. The positioning and retaining system of claim 2, wherein the curved intra-oral sensor is flexible, and wherein the holder is configured to apply a bending force to curve the intra-oral sensor and to hold the intra-oral sensor in its curved shape.

7. A positioning and retaining system for an intra-oral sensor comprising:
   a holder having a main body, the main body being a single, monolithic piece that includes a top surface, a bottom surface disposed opposite the top surface, a first side surface, a second side surface, and an elongate, planar, recessed surface that is recessed relative to the top surface at one end of the main body and extends in an elongate direction between the first side surface and the second side surface;
   a first pin coupled to the main body and spaced laterally from the first side surface away from the main body;
   a second pin coupled to the main body and spaced laterally from the second side surface and away from the main body, the second pin spaced from the first pin along the elongate direction, wherein the recessed surface is disposed between the first and second pins along the elongate direction; and a third pin coupled to the main body.

8. The positioning and retaining system of claim 7, further comprising a curved intra-oral sensor having a lower surface resting on the recessed surface, wherein portions of the intra-oral sensor are in contact with the first and second pins.

9. The positioning and retaining system of claim 7, wherein the third pin is a movable pin that is slidingly coupled to the main body and adapted to move between a first position and a second position along a direction that is perpendicular to the elongate direction of the recessed surface, wherein the second position is closer to the main body than the first position.

10. The positioning and retaining system of claim 7, wherein each of the first, second, and third pins is fixed to the main body.

11. The positioning and retaining system of claim 7, wherein each of the first, second, and third pins is cylindrical.

12. The positioning and retaining system of claim 7, wherein the main body includes a groove along the bottom surface, wherein the positioning and retaining system includes an arm that is configured to slide within the groove, wherein the third pin is directly coupled to the arm.

13. A positioning and retaining system for an intra-oral sensor comprising:

a holder having a main body, the main body being a single piece that includes a top surface, a bottom surface disposed opposite the top surface, and a recessed surface that is recessed relative to the top surface;

an arm slidingly coupled to the main body; and a sliding block coupled to the arm, wherein the sliding block has a convex surface configured to contact an intra-oral sensor and simultaneously press the intra-oral sensor against the main body.

14. The positioning and retaining system of claim 13, further comprising an intra-oral sensor, wherein the intra-oral sensor includes a concave surface in contact with the convex surface of the sliding block, and wherein the intra-oral sensor is pressed against the main body.

\* \* \* \* \*